United States Patent [19]
Sutterlin et al.

[11] Patent Number: 5,261,909
[45] Date of Patent: Nov. 16, 1993

[54] VARIABLE ANGLE SCREW FOR SPINAL IMPLANT SYSTEM

[75] Inventors: Chester E. Sutterlin, Gainesville, Fla.; Richard B. Ashman, Dallas, Tex.

[73] Assignee: Danek Medical, Inc., Memphis, Tenn.

[21] Appl. No.: 836,362

[22] Filed: Feb. 18, 1992

[51] Int. Cl.$^5$ ............................................. A61F 5/04
[52] U.S. Cl. ......................................... 606/61; 606/72; 606/60
[58] Field of Search ................... 606/53, 54, 55, 57, 606/58, 59, 60, 61, 62, 63, 64, 72, 73, 74, 69, 66; 128/69

[56] References Cited

U.S. PATENT DOCUMENTS

| | | | |
|---|---|---|---|
| 4,662,365 | 5/1987 | Gotzen et al. | 606/54 |
| 4,946,458 | 8/1990 | Harms et al. | 606/61 |
| 4,987,892 | 1/1991 | Krag et al. | 606/61 |
| 5,002,542 | 3/1991 | Frigg et al. | 606/61 |
| 5,047,029 | 9/1991 | Aebi et al. | 606/61 |
| 5,127,912 | 7/1992 | Ray et al. | 606/61 |

FOREIGN PATENT DOCUMENTS

| | | | |
|---|---|---|---|
| 140329 | 2/1980 | Fed. Rep. of Germany | 606/59 |
| 3219575 | 5/1982 | Fed. Rep. of Germany | |
| 2090745 | 7/1982 | United Kingdom | 606/65 |

OTHER PUBLICATIONS

"Surgical Technique Manual" by Danek Medical, Inc., published 1990.

Primary Examiner—Danton D. DeMille
Assistant Examiner—David J. Kenealy
Attorney, Agent, or Firm—Woodard, Emhardt, Naughton, Moriarty & McNett

[57] ABSTRACT

A variable angle bone screw system for use in a spinal implant system to connect a vertebral fixation element to a spinal rod extending adjacent the vertebral column in a patient. The system includes an eyebolt having a threaded stem, a washer receivable over the stem of the eyebolt, a bone screw including a yoked head to permit top loading of the stem of the eyebolt, and a nut engaging the threaded stem of the eyebolt and cooperating with the eyebolt to clamp the bone screw and washer therebetween. The bone screw head and the washer include interdigitating locking means for restraining the pivoting of the screw about the axis of the eyebolt threaded stem but permitting interlocking in variable angular orientations.

17 Claims, 4 Drawing Sheets

VARIABLE ANGLE SCREW FOR SPINAL IMPLANT SYSTEM

BACKGROUND OF THE INVENTION

The present invention relates generally to the field of spinal implant systems of the type which employ spinal rods connected at various locations along the spinal column by various fixation elements including spinal screws and, more particularly, to a spinal screw fixation element which provides variable angle adjustability.

Several systems have been developed for use in correcting and stabilizing spinal curves and facilitating spinal fusion. In one system, a bendable rod is longitudinally disposed adjacent the vertebral column and is fixed to various vertebrae along the length of the column by way of a number of fixation elements. A variety of fixation elements can be provided, such as hooks or bone screws, which are configured to engage specific portions of the vertebra.

An example of one such system is the TSRH TM spinal system of Danek Medical, Inc. In this system, the hooks or screws are engaged to the spinal rod by way of eyebolts. As is well known in the art, the eyebolts are received over the spinal rod and captured within a yoke means formed on the head of the fixation hook or screw. A nut is threaded onto a threaded post of the eyebolt to clamp the yoke and to provide a three-point shear clamp force positively locking the hook or screw element to the spinal fixation rod. Details of the TSRH spinal implant system are disclosed in the "Surgical Technique Manual" provided by Danek Medical, Inc., published in 1990, which disclosure is incorporated herein by reference.

It is the goal of the surgeon using such spinal implant systems to apply the vertebral fixation elements (hooks and/or screws) to the spine in the appropriate anatomic position, and then to engage each fixation element to the spinal rod. Once the spinal implant system is assembled it is then possible to correct anatomical deformities and stabilize the spine. In order to perform this procedure with a minimum of patient trauma, it is important that the system used be relatively easy to install. Further, it is highly desirable that the system permit three dimensional adjustment of the bone screw fixation elements in order to take advantage of the most desirable fixation sites in the spinal column. Ideally, a mechanism providing such adjustment should be designed in a manner which does not create undue difficulty in installing the spinal rod or detract from the overall rigidity of the system.

Various mechanisms have been employed in spinal implant systems to provide a three dimensional adjustment capability. U.S. Pat. No. 4,946,458 to Harms et al. discloses a pedicle screw provided with a ball and socket type arrangement for permitting angulation of the bone screw relative to the receiver.

U.S. Pat. No. 4,662,365 to Gotzen el al describes an external bone fixator employing radially splined interdigitation elements to vary the angular orientation of bone screws. However, the arrangement is far too cumbersome and complex for internal fixation to the spinal column.

U.S. Pat. No. 4,987,892 to Krag et al. discloses a spinal fixation system employing pedicle screws having radially splined heads interdigitating with radial splines or teeth integrally formed upon articulating clamps which in turn clamp about a stabilizing rod. The articulating clamp arrangement requires the radial splines be offset relative to the stabilizing rod. This offset creates alignment problems which make it difficult, if not impossible, to permit the screws to be angularly rotated in a plane perpendicular to the axis of the stabilizing rod. Furthermore, the Krag et al. system requires a specially formed articulating clamp for the pedicle screw. If hooks, crosslinks or other fixation elements are to be connected to the stabilizing rod, differently configured rod attachment elements would be needed. This undesirably complicates the overall structure and installation method. Another difficulty of the Krag et al. system is that it is not an open design. In other words, the articulating clamp must be engaged on the rod prior to insertion. On the contrary, a more beneficial design would permit dropping the spinal rod into the screw connector.

German Patent No. 3,219,575 C2 to Kluger discloses a spinal implant system which provides angular adjustment of the bone screws by relative movement of interdigitating disk contact surfaces on corner pieces within which each bone screw is mounted. The system is mechanically complex, in that separate adjusting means are needed to angularly adjust the orientation of the bone screws and to fix the position of the bone screws relative to the corner pieces and to one another. Any rotational adjustment of the bone pins in a plane normal to the spinal rods changes the distance between the pins, requiring further adjustment of the sleeve nut. Further, the system is limited to situations where only two pins or other fixation elements are required on the same rod.

SUMMARY OF THE INVENTION

In one aspect of the present invention, there is provided a variable angle bone screw system for use in a spinal implant system to connect a vertebral fixation element to a spinal rod extending adjacent the vertebral column in a patient. In a preferred embodiment, the system is characterized by an eyebolt including a head defining a passage for receiving the spinal rod therethrough. The eyebolt further includes a threaded stem extending from the head along an axis perpendicular to and intersecting the axis of the spinal rod. A bone screw is provided having a head and a threaded shank adapted to be screw inserted into a portion of a vertebra. In addition, there is a washer having a means for mounting to the eyebolt. The mounting means serves to prevent rotation of the washer relative to the axis of the eyebolt threaded stem. The bone screw head and the washer include interdigitating locking means for restraining the pivoting of the screw about the axis of the eyebolt threaded stem while permitting interlocking in variable angular orientations. The system further has a nut for engaging the threaded stem of the eyebolt, whereby the bone screw and the washer are clamped between the eyebolt head and the nut when the nut is tightened on the threaded stem of the eyebolt.

Accordingly, it is an object of the present invention to provide an improved spinal implant system.

An additional object and benefit of the present invention is served by providing an improved spinal implant system which permits three dimensional adjustment of the bone screw fixation elements without undesirably complicating the overall design of the system or rendering installation of the spinal rod more difficult.

It is a yet further object of the present invention to provide an improved spinal implant system having the above benefits and which affords the further advantage that all spinal rod attachments for screws, hooks, and crosslinks may be made with a universal eyebolt attachment mechanism.

Still another object is met by this invention through the top-loading capability of the variable angle screw. The open configuration of the screw allows insertion of the screw into the pedicle, for example, and then subsequent engagement to an appropriately contoured spinal rod by way of an eyebolt configured in accordance with the present invention.

Related objects and advantages of the present invention will become more apparent by reference to the following drawing figures and detailed description.

DESCRIPTION OF THE PREFERRED EMBODIMENT

Figure 1:
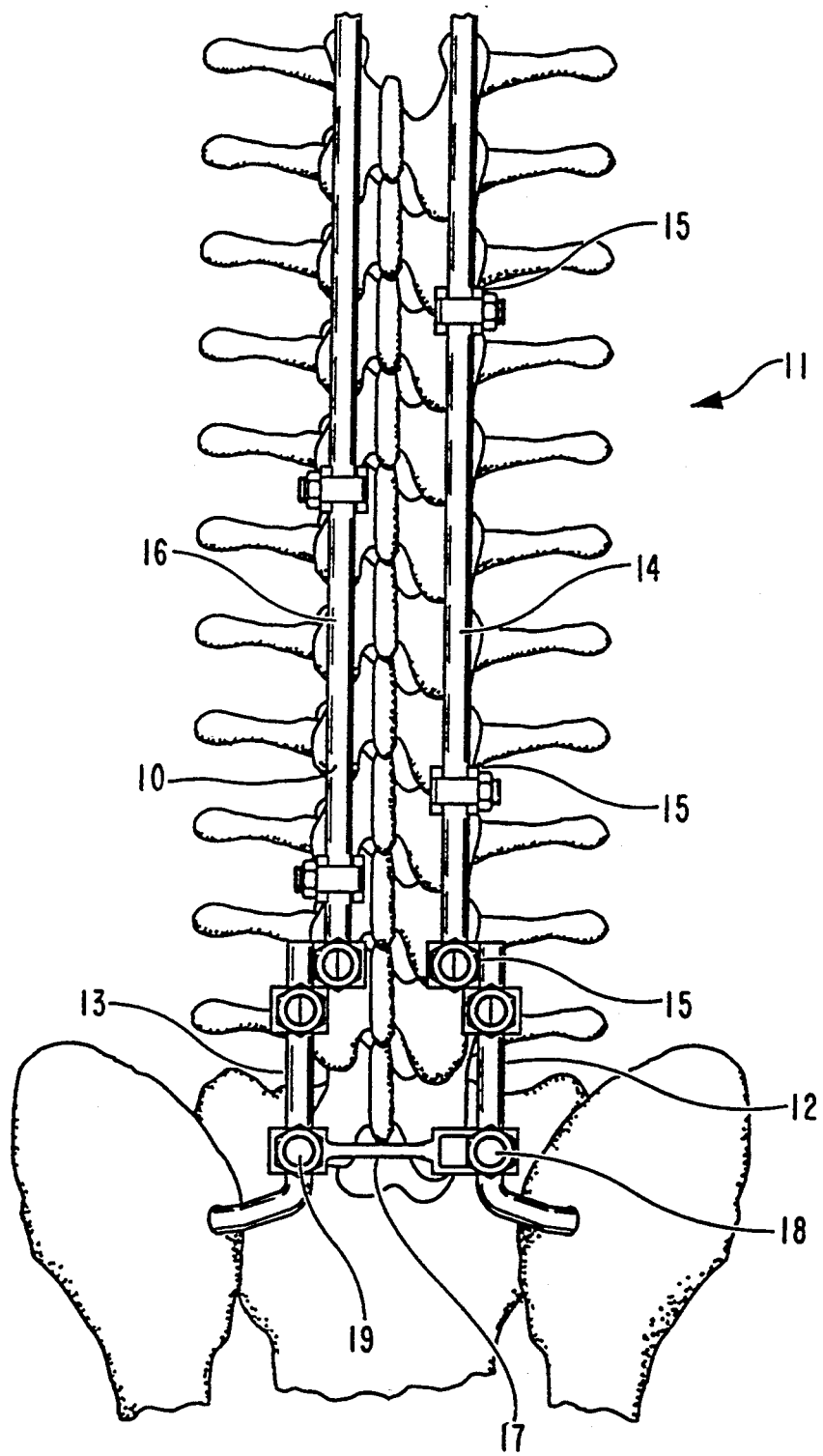
FIG. 1 is a fragmentary posterior view of a spinal column with an implant system incorporating the variable angle bone screw of the present invention.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Referring now to the drawings in detail, FIG. 1 shows part of the pelvis and spinal column generally designated at 11 receiving a spinal implant system 10. The system 10 includes a series of four spinal rods. Two of them, rods 12 and 13, have their lower ends secured in the sacrum while the other two, rods 14 and 16, extend upward along the spinal column. A plurality of bone screws and/or hooks are employed at spaced locations along rods 14 and 16 for connection of the rods to the vertebrae, preferably in the pedicle. In addition, spacer links, screws and/or hooks are connected to the rods 12 and 13. All of the spacers, screws and/or hooks are clamped to the rods by eyebolts For example, the spacer link 17 establishing the space between the rods 12 and 13 at the link location is affixed to the rods 12 and 13 by eyebolts 18 and 19, respectively. The rod 14 is connected to the spinal column by fixation elements 15.

Depending upon a variety of factors, the particular type of spinal fixation element employed may be either a hook type element or a bone screw. If hooks are employed as the fixation elements, the hooks may be constructed in a variety of shapes and sizes such as shown and described in pages 6-10 of the Danek Surgical Technique Manual for the TSRH ™ Spinal Implant System, published by Danek Medical, Inc. of Memphis, Tennessee, on Feb. 1, 1990. All screws, hooks and spacers have in common, a "three-point shear" clamp feature when combined with the eyebolt as described in that manual. It should be appreciated, however, that the bone screw of the previous TSRH ™ Spinal Implant System, such as described in pages 9-10 of that manual, can not vary its angular orientation relative to the rod axis.

Figure 2:
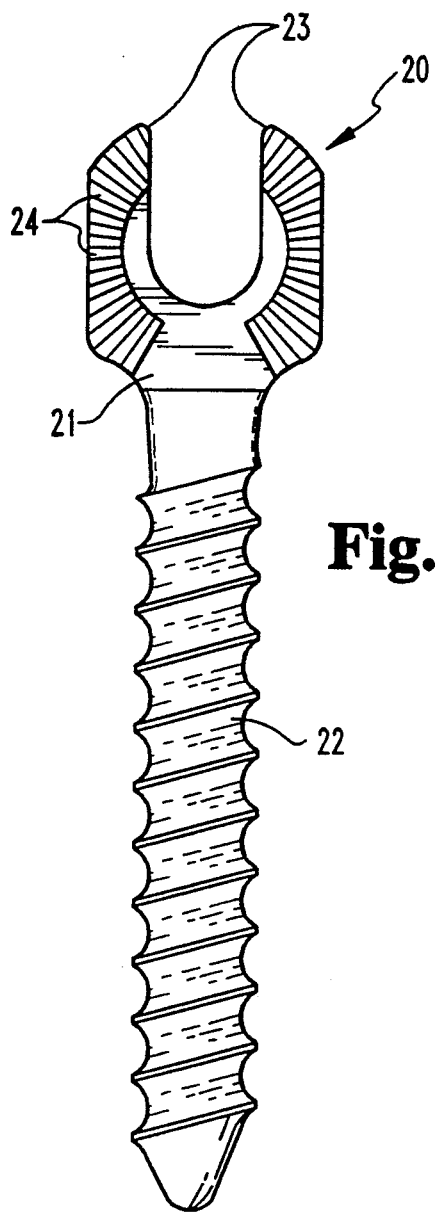
FIG. 2 is an elevational view of the variable angle bone screw of the present invention.

Referring now particularly to FIG. 2, there is shown a preferred construction of the variable angle bone screw 20 of the present invention. The screw 20 has a head 21 and threaded shank 22. In one specific preferred embodiment, the shank 22 is threaded for engaging the pedicle of a vertebra. The head 21 has a U-shape forming an open yoke 23 which receives the threaded stem of an eyebolt. The open yoke 23 provides an advantageous top-loading aspect to the screw 20. One side of the head 21 is formed to define a series of radially extending teeth or splines 24. In the preferred embodiment each spline 24 circumscribes an arc of six degrees. The screws 20 are preferably provided in diameters of 5.5 and 6.5 mm and in lengths ranging from 25 to 50 mm.

Figure 3:
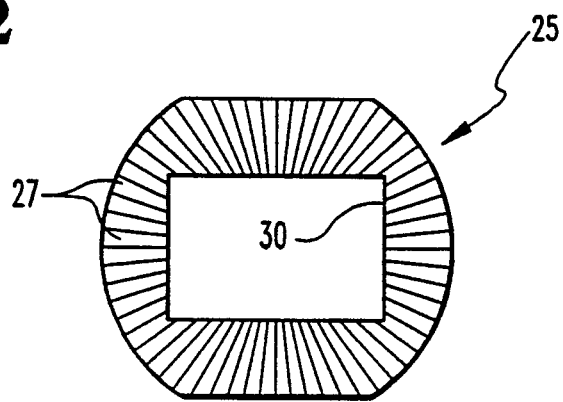
FIG. 3 is an elevational view of the variable angle screw washer.
Figure 4:
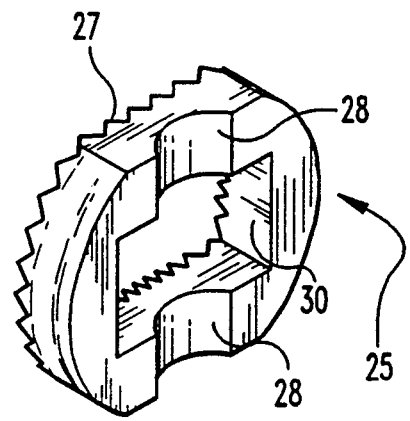
FIG. 4 is a perspective view of the washer of FIG. 3.

FIGS. 3 and 4 depict the variable angle washer 25. One side of the washer 25 defines a series of radially extending teeth or splines 27 which are formed to interdigitate with the splines 24 on a corresponding screw 20. The opposed side of washer 25 defines an axially aligned pair of part cylindrical shaped recesses 28 which receive therein the spinal rod when the washer is mounted thereon. The through opening 30 in washer 25 is rectangularly shaped and sized to permit washer 25 to be received over the head portion of an eyebolt in a close sliding fit.

Figure 5:
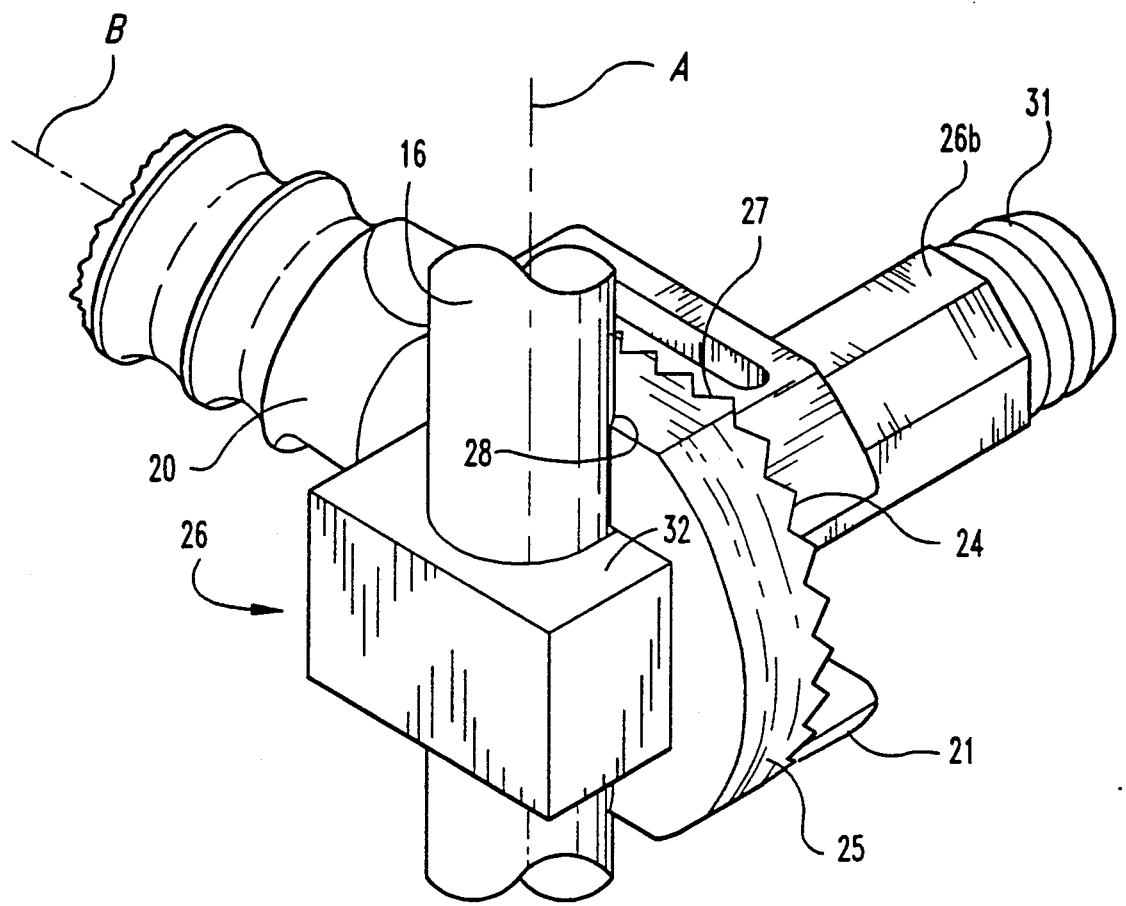
FIG. 5 is a fragmentary perspective view showing the variable angle screw assembly mounted on a spinal rod.

FIG. 5 shows a variable angle screw 20, washer 25 and eyebolt/locknut assembly 26 mounted to a spinal rod 16. Eyebolt/locknut assembly 26 includes eyebolt 26a and locknut 26b. The eyebolt/locknut assembly is a conventionally known spinal rod fastener and may preferably be a ¼ inch eyebolt/locknut assembly provided by Danek Medical, Inc. as part number 808-029 for use with the Danek TSRH ™ Spinal Implant System. Eyebolt 26a is situated at a desired location along rod 16 and washer 25 is mounted onto eyebolt 26a over the threaded stem 31 so that the washer 25 surrounds eyebolt head 32 and abuts rod 16 with the rod 16 received within recesses 28 so as to provide a yoke clamping force which securely fixes the position of eyebolt 26a on rod 16. When in this position, the splines 27 extend from the head 32 a sufficient distance such that with the splines 24 and 27 in interdigitating contact with the head 21 of bone screw 20 can be positioned in any desired angular orientation without interference with head 32. The yoked head 21 of bone screw 20 permits top-loading the stem 31 of the eyebolt 26a onto the screw 20 without having to manipulate the screw or spinal rod to pass the stem through a closed of the screw, as in prior devices such as shown in the aforementioned Krag et al. U.S. Pat. No. 4,987,897. A locknut 26b is threaded over the threaded stem 31 until it contacts the non-splined side of screw 20. As nut 26b is tightened, it pushes the screw 20 and washer 25 towards the rod 16 so that the rod 16 will be clamped between the eyebolt 26a and washer 25 in the manner of a three-point shear clamp.

Because of the interdigitated connection between the washer 25 and screw 20 the angular orientation between the rod axis A and screw axis B can be varied as desired, and it is no longer necessary that the spinal rod be bent to accommodate angulations other than perpendicular. Further, variable angle screws 20 may be mounted to the spinal rod using the same eyebolt fasteners as are used to mount other fixation elements such as hooks and spacers, thus reducing the number of different parts and simplifying the installation procedure. In addition to varying the angular orientation of the screws 20 in a plane parallel to the rod by relative rotation of the interdigitating splines, it is possible to vary the angular orientation of the screws in a plane transverse to the axis of the rod by pivoting the threaded stem of the eyebolt relative to the spinal rod.

Figure 6:
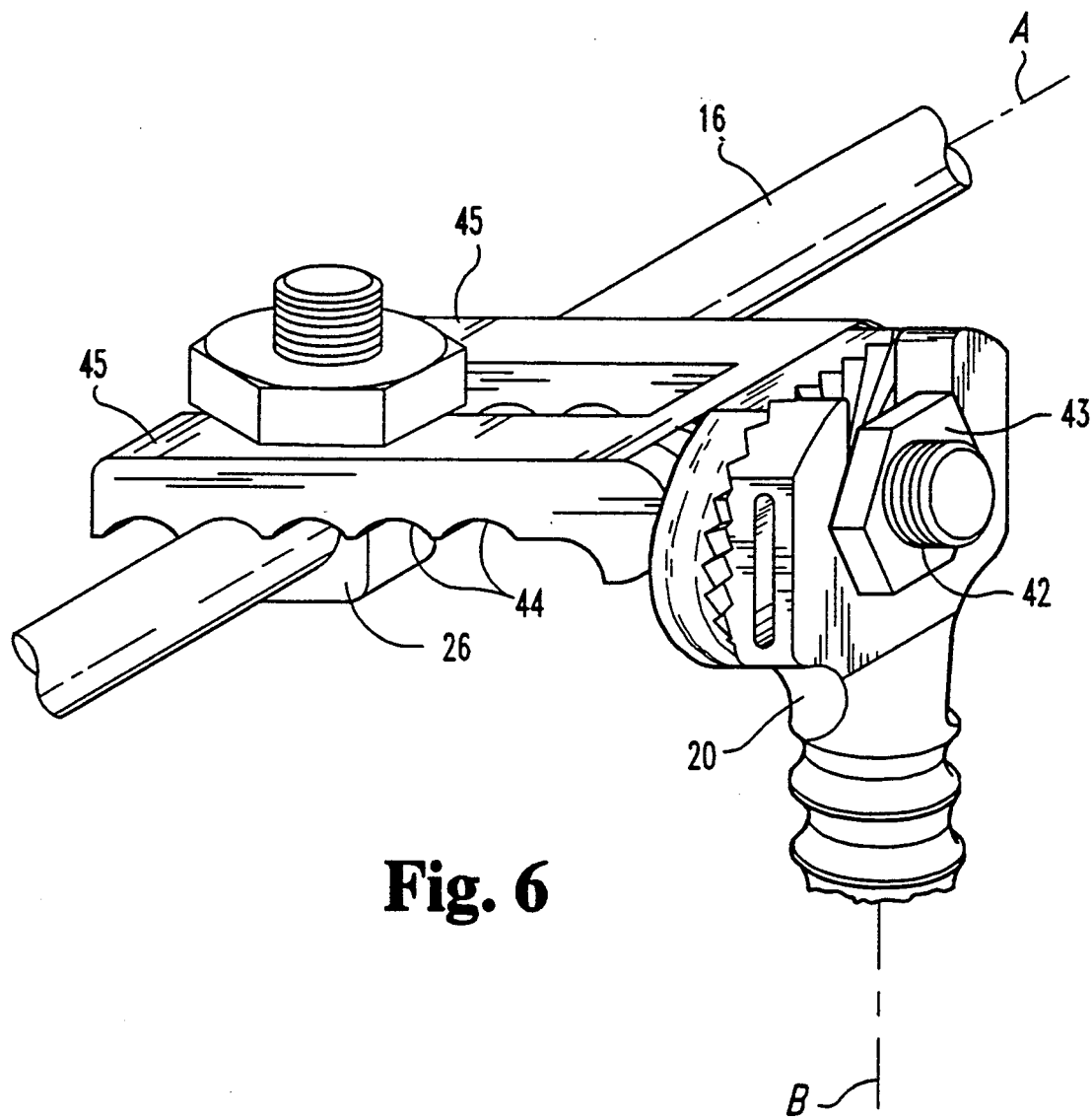
FIG. 6 is a fragmentary perspective view showing the variable angle screw assembly mounted on a spinal rod via a lateral offset connector.

In addition to direct mounting to an eyebolt/locknut assembly 26, the variable bone screw of the present invention may be mounted to a lateral offset connector of the type disclosed in U.S. Patent application Ser. No. 07/803,325 filed Dec. 4, 1991 entitled Lateral Offset Connector for Spinal Implant System which is hereby incorporated herein by reference. FIG. 6 shows an offset connector 40 mounted to a spinal rod 16 by an eyebolt/locknut assembly 26. The connector 40 includes a pair of arms 45 which serve as a yoke clamping eyebolt 26 and preventing its movement along rod 16. The washer 25 and variable angle bone screw 20 are mounted to a guide portion having a rectangular shape for receiving the washer and a threaded post 42 extending therefrom. Alternatively, the washer 25 may be dispensed with as a separate element and its radial splines may be integrally incorporated into the connector 40 at the base of threaded post 42. A locknut 43 secures the position of the bone screw 20. The lateral offset of screw 20 relative to rod 16 may be selectively adjusted by selective positioning of rod 16 in pairs of aligned grooves 44, thereby accommodating abnormal lateral curvatures of the spine in the saggital plane.

It is apparent from the foregoing that the present invention provides a variable angle screw that can be engaged within the pedicle of a vertebra and then subsequently fastened to a contoured spinal rod without requiring the excessive manipulation characteristic with prior similar devices. The spinal screw 20 of the present invention combines a top-loading feature with the capability for interdigitated engagement with the spinal rod to accommodate varying angles of the screw relative to the rod.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected. For example, in a specific embodiment, the washer 25 may be trapped on the eyebolt 26a, such as by swaging a retainer onto the threaded stem 31. In this manner, the washer 25 can be loosely retained on the eyebolt until its splined surface engages the corresponding splined surface of the bone screw 20. Retaining the washer on the eyebolt reduces the number of loose pieces that must be manipulated during an implant procedure.

What is claimed is:

1. A variable angle bone screw system for use in a spinal implant system to connect a vertebral fixation element to a spinal rod extending adjacent the vertebral column in a patient, comprising:

an eyebolt including a head defining a passage for receiving said spinal rod therethrough, said eyebolt further including a threaded stem extending from said head along an axis perpendicular to and intersecting the axis of said spinal rod;

a bone screw having a head and a threaded shank adapted to be screw inserted into a desirable vertebral fixation site;

a washer having a means for mounting to said eyebolt, said mounting means preventing rotation of said washer relative to the axis of said eyebolt threaded stem, said bone screw head and said washer including interdigitating locking means for restraining the pivoting of said screw about the axis of said eyebolt threaded stem but permitting interlocking in variable angular orientations; and a nut for engaging said threaded stem of said eyebolt, whereby said bone screw and said washer are clamped between said eyebolt head and said nut when said nut is tightened on said threaded stem of said eyebolt.

2. The variable angle bone screw system of claim 1, wherein said washer includes a curved recess arranged to contact the spinal rod when the rod is clamped between said eyebolt head and said nut.

3. The variable angle bone screw system of claim 1 wherein said bone screw head includes a yoke portion defining an opening in which to receive said eyebolt threaded stem to permit top loading of the eyebolt onto the bone screw.

4. The variable angle bone screw system of claim 1 wherein said securing means of said washer includes a rectangular shaped opening defined by said washer, said opening being sized to permit said eyebolt head to be closely received within said opening.

5. The variable angle bone screw system of claim 1 wherein said threaded shank of the bone screw includes thread configured to engage the pedicle of a vertebra.

6. A spinal implant system, comprising:

at least one spinal rod adapted to extend adjacent the vertebral column in a patient;

a plurality of eyebolt/locknut assemblies;

a plurality of hooks and screws for connecting a plurality of vertebral elements in said vertebral column to said at least one spinal rod via said eyebolt/locknut assemblies, each of said eyebolt/locknut assemblies having an eyebolt including a head defining a passage for receiving a spinal rod therethrough, said eyebolt further including a threaded stem extending from said head along an axis perpendicular to and intersecting the axis of said spinal rod and a locknut for engaging said threaded stem;

a variable angle bone screw having a head and a threaded shank adapted to be inserted into a vertebral element;

a washer having a means for mounting to said eyebolt, said mounting means preventing rotation of said washer relative to the axis of said eyebolt threaded stem, said head of said bone screw and said washer including interdigitating locking means for restraining the pivoting of said bone screw about the axis of said eyebolt threaded stem but permitting interlocking in variable angular orientations, whereby said bone screw and said washer are clamped between said eyebolt head and said locknut when said locknut is tightened on said threaded stem.

7. The spinal implant system of claim 6 wherein said mounting means of said washer includes a rectangular shaped opening defined by said washer, said opening being sized to permit said washer to be closely received over said eyebolt head.

8. The spinal implant system of claim 7 wherein said bone screw head includes a yoke portion defining an opening in which to receive said eyebolt threaded stem to permit top loading of the eyebolt onto the bone screw.

9. The spinal implant system of claim 8, wherein said washer includes a curved recess arranged to contact the spinal rod when the rod is clamped between said eyebolt head and said nut.

10. The spinal implant system of claim 6, wherein said threaded shank of said bone screw includes threads configured for engaging the pedicle of a vertebra.

11. A variable angle bone screw system for use in a spinal implant system to connect a vertebral fixation element to a spinal rod extending adjacent the vertebral column in a patient, comprising:
   an eyebolt including a head defining a passage for receiving said spinal rod therethrough, said eyebolt further including a threaded stem extending from said head along an axis perpendicular to and intersecting the axis of said spinal rod;
   a bone screw having a head and a threaded shank adapted to be screw inserted into a desirable vertebral fixation site;
   a yoke clamping means for fixing the mounting of said eyebolt to the rod;
   an interdigitating locking means, associated with said bone screw, for restraining the pivoting of said screw about the axis of said eyebolt threaded stem but permitting interlocking of said bone screw and said yoke clamping means in variable angular orientations; and
   a nut for engaging said threaded stem of said eyebolt, whereby said bone screw and said yoke clamping means are clamped between said eyebolt head and said nut when said nut is tightened onto said threaded stem of said eyebolt.

12. The variable angle bone screw system of claim 11 wherein said yoke clamping means is a washer having aligned curved recesses.

13. The variable angle bone screw system of claim 11 wherein said yoke clamping means includes a lateral offset connector which serves to laterally offset the position of said bone screw relative to said rod.

14. The variable angle bone screw system of claim 13 wherein said lateral offset connector includes a pair of laterally extending arms.

15. The variable angle bone screw system of claim 11 wherein said interdigitating locking means includes a plurality of intermeshing radially spaced apart splines on said washer and said bone screw.

16. The variable angle bone screw system of claim 1 wherein said interdigitating locking means includes a plurality of intermeshing radially spaced apart splines on said washer and said bone screw.

17. The spinal implant system of claim 6 wherein said interdigitating locking means includes a plurality of intermeshing radially spaced apart splines on said washer and said bone screw.

* * * * *

UNITED STATES PATENT AND TRADEMARK OFFICE
CERTIFICATE OF CORRECTION

PATENT NO. : 5,261,909

DATED : November 16, 1993

INVENTOR(S) : Chester E. Sutterlin and Richard B. Ashman

It is certified that error appears in the above-identified patent and that said Letters Patent is hereby corrected as shown below:

In Column 3, at line 19, "hone" should read --bone--.

Signed and Sealed this

Twenty-seventh Day of September, 1994

Attest:

BRUCE LEHMAN

Attesting Officer

Commissioner of Patents and Trademarks